United States Patent [19]

Rogozinski

[11] Patent Number: 5,573,537
[45] Date of Patent: Nov. 12, 1996

[54] INSTRUMENT FOR PROBING AND REAMING A PEDICLE

[76] Inventor: Chaim Rogozinski, 3223 Front Rd., Jacksonville, Fla. 32217

[21] Appl. No.: 386,765

[22] Filed: Feb. 10, 1995

[51] Int. Cl.⁶ .................................................. A61B 17/00
[52] U.S. Cl. .......................... 606/80; 606/79; 408/225
[58] Field of Search .................................. 606/79, 80, 81, 606/86, 96, 97, 98, 72, 73, 61; 408/225, 224

[56] References Cited

U.S. PATENT DOCUMENTS

| | | | |
|---|---|---|---|
| 1,911,764 | 5/1933 | Martin | 606/80 |
| 2,494,229 | 1/1950 | Collison | 606/73 |
| 4,590,929 | 5/1986 | Klein | 606/80 |
| 4,978,350 | 12/1990 | Wagenknecht | 606/72 |
| 5,161,726 | 11/1992 | Francis | 408/225 |
| 5,190,548 | 3/1993 | Davis | 606/80 |
| 5,326,196 | 7/1994 | Noll | 408/225 |

FOREIGN PATENT DOCUMENTS 2074061  10/1981  United Kingdom .................. 408/225

*Primary Examiner*—Michael Powell Buiz
*Assistant Examiner*—Kevin Truong
*Attorney, Agent, or Firm*—Edward S. Irons

[57] ABSTRACT

A unitary instrument for providing a step-down screw hole in a pedicle is provided. The tool includes an end member for rotatable connection with a power source, the probe for providing a pilot hole in the pedicle and a side-cutting reamer member for providing an anchor hole for a pedicle screw positioned about the pilot hole. The arrangement is such that the instrument is self-centering in part due to the presence of the probe in the pilot hole.

2 Claims, 3 Drawing Sheets

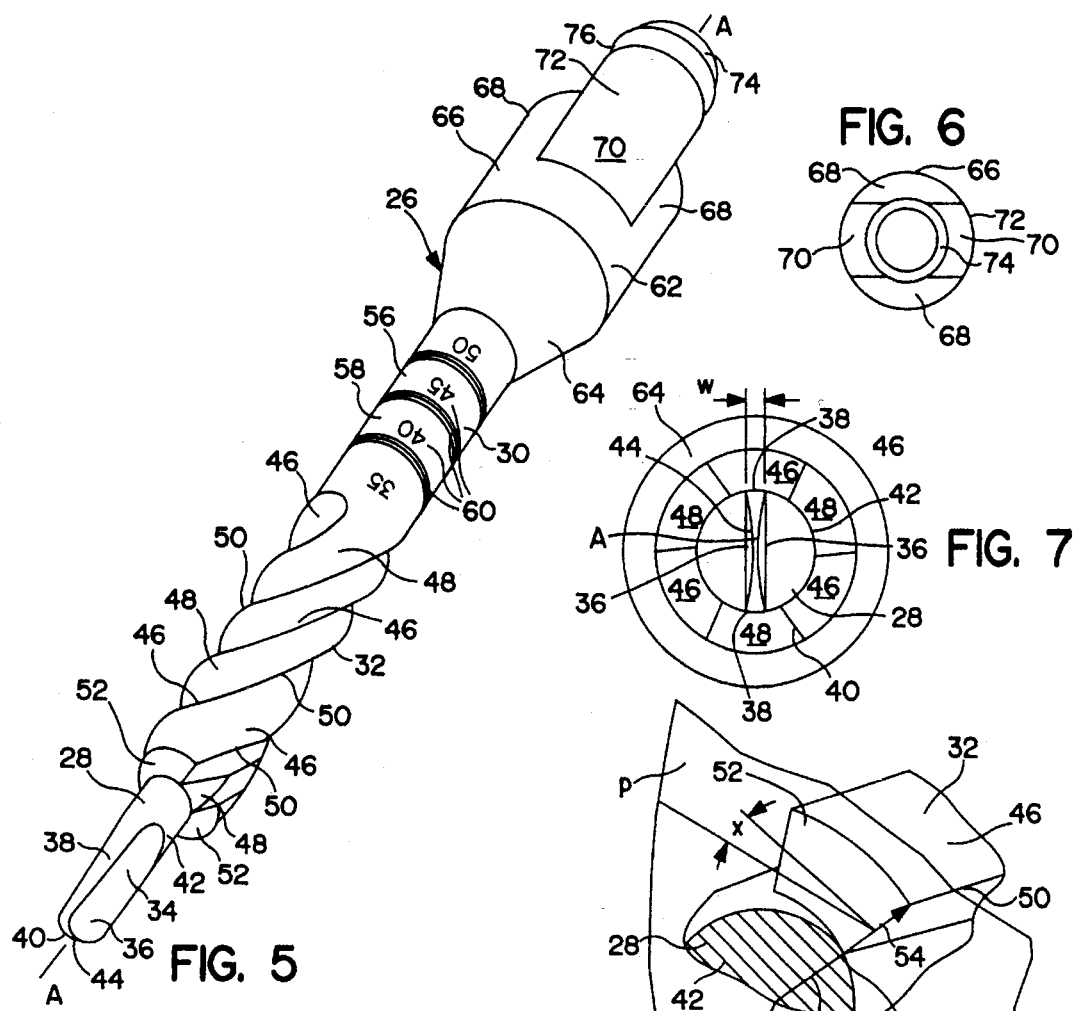

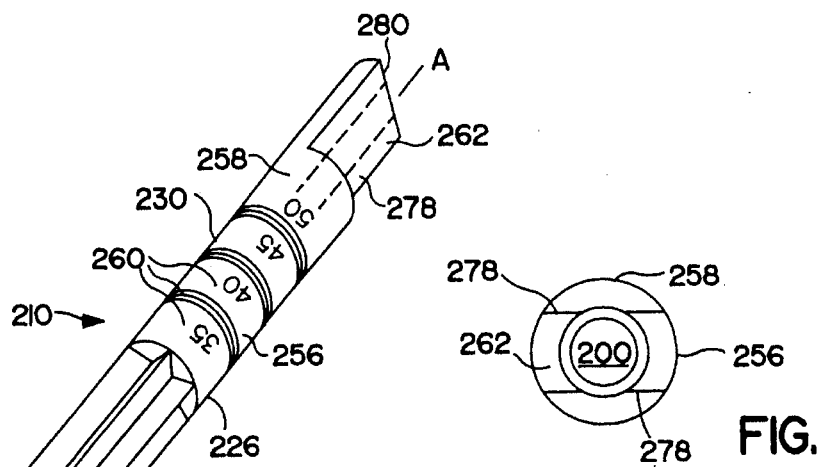
FIG. 11
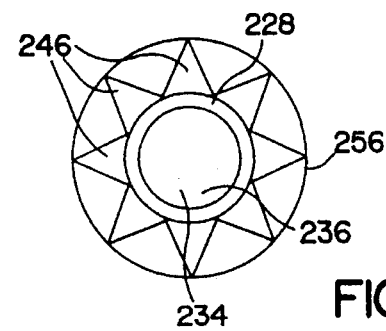
FIG. 12
FIG. 13
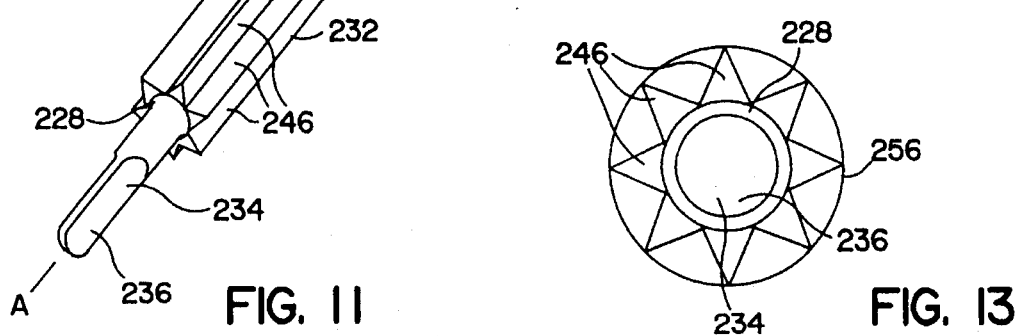
FIG. 14
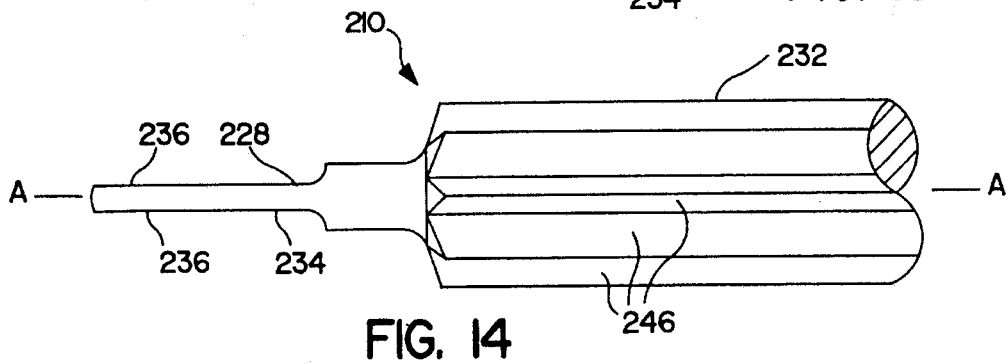
FIG. 15
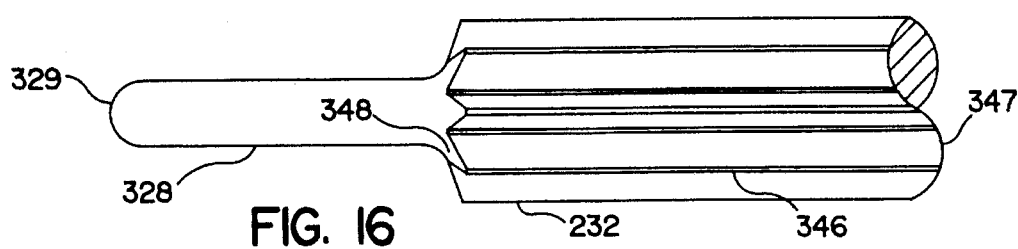
FIG. 16

INSTRUMENT FOR PROBING AND REAMING A PEDICLE

FIELD OF THE INVENTION

This invention relates to a combined pedicle reamer and probe. In use, the device forms a step-down hole in a pedicle in which the probe self-centers, thus reducing the number of operative steps required to insert pedicle screws.

BACKGROUND OF THE INVENTION

Injury or disease may require surgery to immobilize a spinal segment. Conventional immobilization techniques require screw fixation of rods or plates to pedicles.

Known techniques include pedicle screw insertion steps for probing, drilling, inserting X-ray markers, imaging and tapping. For example, pursuant to one common surgical technique:

(1) optimum location of the pedicle screw is determined by inserting a probe into a pilot hole in the pedicle, (2) the pilot hole is reamed with a front cutting bit to form a pedicle screw anchor hole, (3) an X-ray marker is inserted into the anchor hole, and X-rays are taken to assure that the anchor hole is properly positioned, formed, and of an appropriate depth to accommodate the required pedicle screw length, (4) the anchor hole is tapped by providing threads in its sidewall, and (5) a pedicle screw is screwed into the tapped anchor hole.

Such techniques are attended by a plurality of disadvantages including significant risk of nerve root injury.

SUMMARY OF THE INVENTION

This invention provides a novel combination reaming and probing instrument and a method for its use to install pedicle screws. Use of the instrument pursuant to the method of the invention reduces the number of operative steps required for correct pedicle screw installation with attendant minimal risk of nerve root injury occasioned by pedicle wall penetration.

It is an important feature of the instrument of the invention that a leading pilot hole can be formed and subsequently reamed to provide an anchor hole in which the probe self-centers. Self-centering is facilitated because the relatively hard cortical outer portion of the pedicle deflects the reamer and probe element of the instrument into the relatively softer cancellous inner portion.

The combination probe and reamer instrument has a quick disconnect distal end, such that it may be permitted to remain in the step-down hole as an X-ray marker in the pedicle. The instrument is calibrated so that the depth of the step-down hole being formed in the pedicle can be visually determined by an operator while the combination probe and reamer tool element is in a stationary condition.

Accordingly, a combination probe and reamer tool element of the present invention is hereinafter described. The combination probe and reamer tool element is adapted for use with a drill device so that, when rotational movement is imparted by the drill device to the combination probe and reamer tool element while a force urges the combination probe and reamer tool element into a pedicle of spinal vertebrae, a step-down hole extending a pre-selected depth from a surface is formed. The step-down hole includes a leading pilot hole having a selected first diameter and a selected fixed depth and a trailing anchor hole immediately following the pilot hole and having a selected second diameter greater than the selected first diameter and a selected variable depth.

The combination probe and reamer tool element of the present invention comprises a preferably unitary elongated structure fabricated from a rigid material, e.g., stainless steel, which extends longitudinally along and centrally about a longitudinal axis. The elongated structure includes a probe member, an end member and a side-cutting reamer member disposed between and connected to said probe member and to said end member.

The probe member may have a blade portion defined by a pair of oppositely disposed sidewalls and a pair of oppositely disposed parallel side edges and terminates in a curved end. The curved end is operative in a rotating condition about the longitudinal axis to form the leading pilot hole into the workpiece. In lieu of the blade portion, the probe may have a generally cylindrical or cone-shaped portion with a rounded tip.

The reamer member is operative in the rotating condition about the longitudinal axis to form the trailing anchor hole into the workpiece. The end member is sized and adapted to be releasably connected to the drill device and to be at least partially received by the trailing anchor hole.

The probe member includes an elongated, preferably cylindrical portion disposed between and connected to the reamer member and the blade portion or the generally cylindrical or cone-shaped portion.

In probes having a blade portion, the two sidewalls are disposed to taper toward the curved end. The curved end of the blade portion includes a curved end face having a face width in a range of 0.005 millimeters and 0.025 millimeters. Each of the side edges in cross-section has a curved outer surface. It is preferred that each of the curved outer surfaces is curved at a constant radius of curvature relative to and about the longitudinal axis with the constant radius of curvature being equal to one half of the selected first diameter of the leading pilot hole.

The reamer member includes a plurality of cutting elements and a plurality of channels. The channels may be provided with undercut areas, not shown, for easy removal of debris. The cutting elements and the channels are arranged in a manner whereby consecutive ones of the cutting elements are separated from one another by respective ones of the channels disposed therebetween. Each of the cutting elements has a lateral cutting edge extending at a selected radial distance from the longitudinal axis. The selected radial distance is preferably equal to one half of the selected second diameter of the trailing anchor hole. Each of the cutting elements may be configured in a shape of a helix or to extend parallel with the longitudinal axis. Preferably, each of the cutting elements of the reamer includes a chamfered face which commences at a location where the probe member and the reamer member are connected and slope toward the end member. Each of the chamfered faces has a forward cutting edge and is formed at an angle relative to an imaginary plane extending radially from the longitudinal axis in a range between 15 degrees and 45 degrees and beveled in such a way as that it is not front cutting.

The end member includes a longitudinally extending cylindrical portion connected to the reamer member. The cylindrical portion is sized and adapted to be slidably received by the trailing anchor hole. The cylindrical portion has an outer cylindrical surface having indicia formed thereon. The indicia represents a plurality of incremental linear measurements with each linear measurement commencing from the curved end of the probe member and ending at a respective one of the indicia. The indicia is operative to indicate linear measurement of the total length of the tool within the bone hole so that an operator can read the indicia proximate to the surface of the workpiece as the elongated structure rests in a stationary condition in and extends from the step-down hole. The end member includes a connecting end portion connected to the cylindrical portion at one end and is operative at an opposite end to releasably engage a mating end portion of the drill device so that the elongated structure can be either connected to or disconnected from the drill device.

These and other aspects of the present invention will become more readily appreciated and understood from consideration of the following detailed description of the exemplary embodiments when taken in conjunction with the accompanying drawings, in which:

BRIEF DESCRIPTION OF THE DRAWINGS

FIG. 5 is a perspective view of a first exemplary embodiment of the combination probe and reamer tool element of the present invention shown in FIGS. 1–4.

FIG. 6 is a perspective view of an alternative round-tipped, generally cylindrical probe member attached to a reamer element as depicted by FIG. 11.

FIG. 7 is an enlarged front view in elevation of the combination probe and reamer tool element of the present invention shown in FIG. 5.

FIG. 8 is an enlarged partial plan view of the probe member and reamer member of the combination probe and reamer tool element of the present invention shown in FIG. 5.

FIG. 9 is a side view in elevation of the combination probe and reamer tool element of the present invention shown in FIG. 5.

FIG. 10 is an enlarged partial perspective view illustrating relief of one cutting member relative to a forward cutting edge thereof.

FIG. 11 is a perspective view of a second exemplary embodiment of the combination probe and reamer tool element of the present invention.

FIG. 12 is a rear view in elevation of the combination probe and reamer tool element of the present invention shown in FIG. 11.

FIG. 13 is an enlarged front view in elevation of the combination probe and reamer tool element of the present invention shown in FIG. 11.

FIG. 14 is an enlarged partial plan view of the probe member and reamer member of the combination probe and reamer tool element of the present invention shown in FIG. 11.

FIG. 15 is a side view in elevation of the combination probe and reamer tool element of the present invention shown in FIG. 11.

FIG. 16 is a perspective view of an alternative round-tipped, generally cone-shaped probe member.

DETAILED DESCRIPTION OF THE EXEMPLARY EMBODIMENTS

Figure 1:
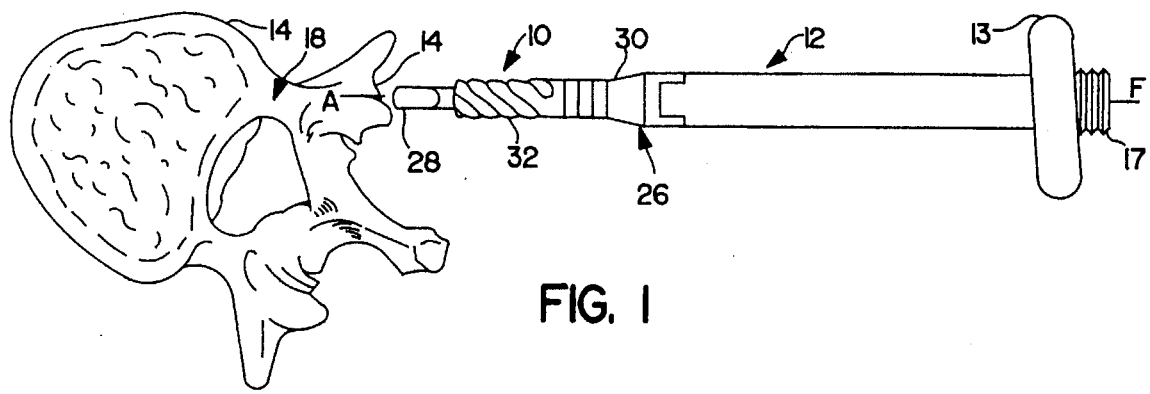
FIG. 1 is a side view in elevation of a combination probe and reamer tool element of the present invention connected to a conventional drill device and disposed proximate to a pedicle of a spinal vertebrae in preparation of forming a step-down hole into the pedicle.

The invention provides a combination probe and reamer tool element adapted for use with a drill device which self-centers in a step-down hole formed in a workpiece, such as a pedicle. As the detailed description of the exemplary embodiments proceeds, a skilled artisan would appreciate that such a self-centering step-down hole can be formed in a variety of workpieces. However, the combination probe and reamer tool element is particularly useful in the medical field for drilling self-centering step-down holes in pedicles of spinal vertebrae during spinal fixation surgery. Thus, when referring to the workpiece in the description as well as in the drawings, the skilled artisan can envision the workpiece as a pedicle of spinal vertebrae. Furthermore, the combination probe and reamer tool element is adapted for use with any conventional drill device which could be either a manually operated one or a power operated one. Furthermore, although not by way of limitation, it is preferable that the combination probe and reamer tool element be adapted for a conventional drill device having a quick connect and disconnect assembly. One of ordinary skill in the art appreciates that a wide variety of quick connect and disconnect assemblies have been developed and are currently being used in industry. Therefore, no further discussion is deemed necessary relating to quick connect and disconnect assemblies and how the combination probe and reamer tool element is releasably connected to the drill device. Additionally, the combination probe and reamer tool element can also be adapted to connect to any common drill device having any conventional releasable connect assembly such as a conventional chuck assembly.

Figure 2:
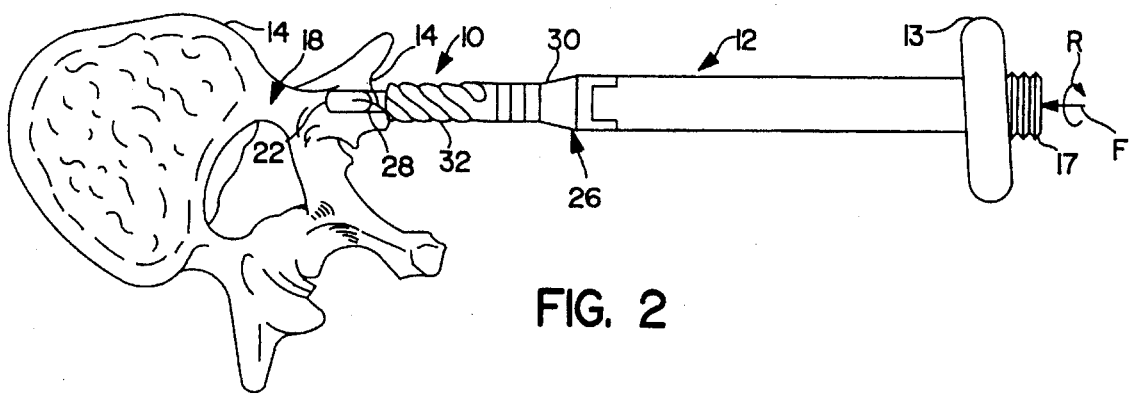
FIG. 2 is a side view in elevation of the combination probe and reamer tool element of the present invention connected to the drill device showing a probe member forming a leading pilot hole into the pedicle.
Figure 3:
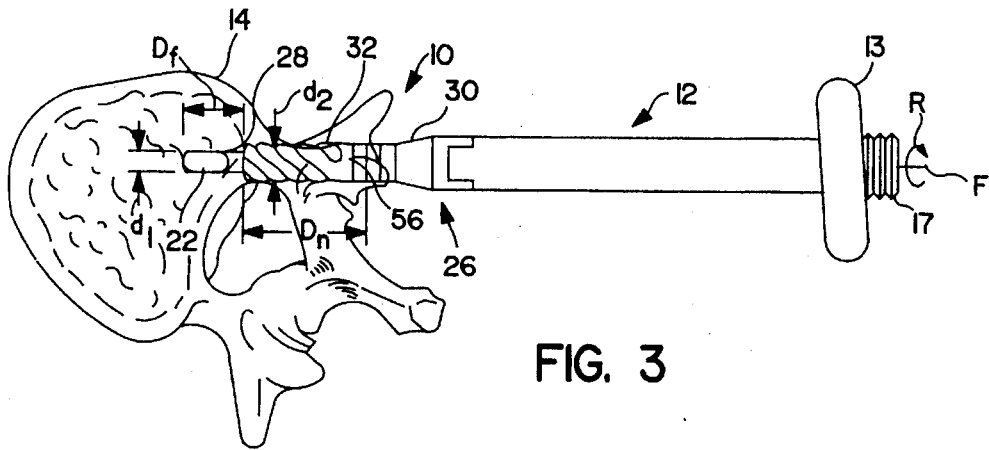
FIG. 3 is a side view in elevation of the combination probe and reamer tool element of the present invention connected to the drill device showing the probe member forming the leading pilot hole into the pedicle, a cutting member of the combination probe and reamer tool element forming a trailing anchor hole into the pedicle which immediately follows the leading pilot hole thereby forming a step-down hole and an end member indicating the linear depth of the step-down hole.
Figure 4:
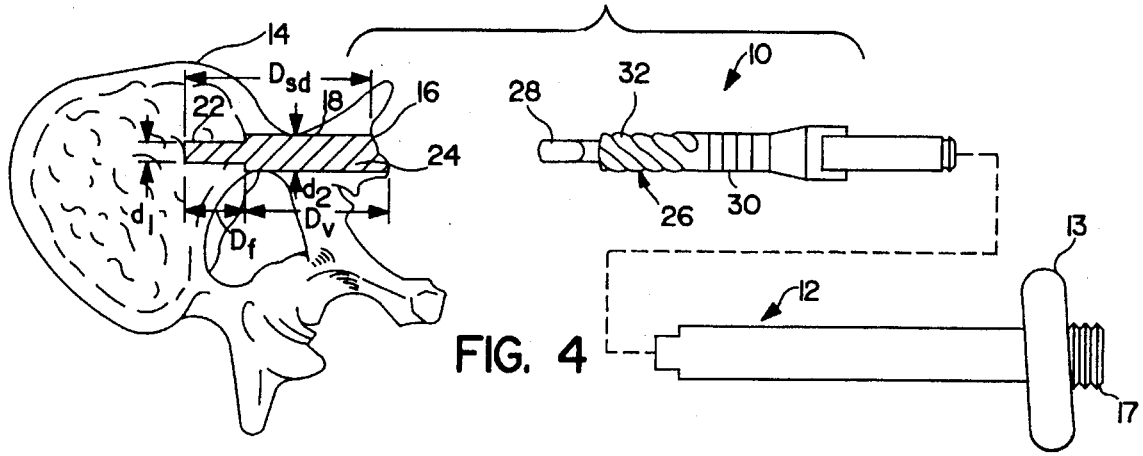
FIG. 4 is a side view in elevation of the combination probe and reamer tool element of the present invention disconnected from the drilling device and showing the step-down hole formed into the pedicle.

A combination probe and reamer tool element 10 is generally introduced in FIGS. 1–10. With reference to FIGS. 1–4, combination probe and reamer tool element 10 is adapted for use with a drill device 12 which is illustrated as a manual drill device with handle 13 and a conventional built-in quick connect and disconnect assembly (not shown) that is operative with knob 17. As shown in FIGS. 2 and 3, when rotational movement "R" is imparted by drill device 12 to combination probe and reamer tool element 10 while a force "F" urges combination probe and reamer tool element 10 into a pedicle 14, a step-down hole 16, as best shown in FIG. 4, extending from a surface 18 of pedicle 14 and to a selected step-down depth "$D_{sd}$" is formed into pedicle 14. Step-down hole 16 includes a leading pilot hole 22 having a selected first diameter "$d_1$" and a selected fixed depth "$D_f$" and a trailing anchor hole 24 immediately following leading pilot hole 22 and having a selected second diameter "$d_2$" greater than selected first diameter "$d_1$" and a selected variable depth "$D_v$."

As best shown in FIGS. 1–9, combination probe and reamer tool element 10 of a first exemplary embodiment of the present invention comprises an elongated structure 26 fabricated of a unitary construction and from a rigid material such as metal. Elongated structure 26 extends longitudinally along and centrally about a longitudinal axis "A" and includes a probe member 28, an end member 30 and a side-cutting reamer member 32 disposed between and connected to probe member 28 and end member 30.

Particularly with reference to FIGS. 5–9, probe member 28 has a blade portion 34 defined by a pair of oppositely disposed sidewalls 36 and a pair of oppositely disposed parallel side edges 38. Blade portion 34 terminates in a curved end 40 which is operative when in a rotating condition about longitudinal axis "A" to form leading pilot hole 22 into pedicle 14. In lieu of the blade portion 34, the probe member 28 may be generally cone-shaped or a cylindrical member. See FIG. 16.

Probe member 28 includes a cylindrical probe portion 42 which is disposed between and connected to blade portion 34 and side-cutting reamer member 32 Probe length "$l_p$" includes blade portion 34 and cylindrical probe portion 42. A skilled artisan would appreciate that fixed depth "$D_f$" of leading pilot hole 22 is equal to probe length "$l_p$" and if a greater fixed depth "$D_f$" is required, a longer probe length "$l_p$" must be employed. Although not by way of limitation, pair of sidewalls 36 of blade portion 34 are disposed to taper toward curved end 40 as best shown in FIG. 8. Curved end 40 includes a curved end face 44 which has a face width "w" as shown in FIGS. 7 and 8. It is preferred for the first exemplary embodiment of combination probe and reamer tool element 10 of the present invention that face width "w" be in a range of 0.005 millimeters and 0.025 millimeters.

In FIG. 7, each of side edges 38 as viewed in cross-section has a curved outer surface. For the first exemplary embodiment of combination probe and reamer tool element 10 of the present invention, each of the curved outer surfaces is curved at a constant radius of curvature "r" relative to and about longitudinal axis "A". One of ordinary skill in the art would appreciate that constant radius of curvature "r" is equal to one half of selected first diameter "$d_1$" of leading pilot hole 22.

Side-cutting reamer member 32 is operative when in a rotating condition about longitudinal axis "A" to form trailing anchor hole 24 into pedicle 14. Reamer member 32 includes a plurality of cutting elements 46 and a plurality of channels 48. Cutting elements 46 and channels 48 are arranged in a manner whereby consecutive ones of said cutting elements 46 are separated from one another by respective ones of channels 48 disposed therebetween. As best shown in FIG. 10, each of cutting elements 46 has a lateral cutting edge 50 extending at a selected radial distance "$r_d$" from longitudinal axis "A". It is appreciated that selected radial distance "$r_d$" is equal to one half of selected second diameter "$d_2$" of trailing anchor hole 24. For the first exemplary embodiment of combination probe and reamer tool element 10, each of cutting elements 46 is configured in a shape of a helix. Each of cutting elements 46 includes a chamfered face 52 as shown in FIG. 8 and 10. Each chamfered face 52 commences at a location "m" where probe member 28 and side-cutting reamer member 32 are connected and slopes toward end member 30. In FIG. 8, chamfered face 52 is formed at an angle relative to an imaginary plane "p" extending radially from longitudinal axis "A" in a range between 15 degrees and 45 degrees. Although not preferred, each of chamfered faces 52 may have a forward cutting edge 54. As shown in FIG. 10, relief at a relief angle "x" is provided for each of chamfered faces 52 relative to imaginary plane "p". Relief angle "x" is preferred to be 18 degrees although relief angle "x" could be in a range of 10 degrees and 30 degrees.

End member 30 is adapted to be releasably connected to drill device 12 (FIGS. 3 and 4) and to be at least partially received by trailing anchor hole 24 (FIG. 3). End member 30 includes a longitudinally extending cylindrical portion 56 which is connected to reamer cutting member 32 as shown in FIGS. 5 and 9. Cylindrical portion 56 is sized and adapted to be slidably received by trailing anchor hole 24 as illustrated in FIG. 3. Cylindrical portion 56 has an outer cylindrical surface 58 which has indicia 60 formed thereon. Indicia 60 represents a plurality of incremental linear measurements shown by way of example only in the FIGS. 5 and 9 by lines extending circumferentially about outer cylinder surface 58 and numerals. For purposes of the first exemplary embodiment of combination probe and reamer tool element 10 of the present invention, each linear measurement commences from curved end 40 of probe member 28 and ends at a respective one of indicia 60 represented, in part, as circumferential lines. A skilled artisan would appreciate that the respective numerals represent the linear measurement. For example, the number "45" represents 45 millimeters from curved end 40 to the circumferential line proximate to the number "45". Specifically, indicia 60 are operative to indicate the linear measurement of selected step-down depth "$D_{sd}$" of the step-down hole 16. An operator can read indicia 60 proximate to surface 18 of workpiece 14 as elongated structure 26 rests in a stationary condition in and extends from step-down hole 16 as shown in FIG. 3.

With reference to FIGS. 5, and 9, end member 30 also includes a connecting end portion 62 which is connected to cylindrical portion 56 at one end and operative at an opposite end to releasably engage a mating end portion of drill device 12 having a conventional quick connect and disconnect assembly (FIGS. 3 and 4). Connecting end portion 62 enables elongated structure 26 to be releasably connected to or disconnected from drill device 12. Connecting end portion 62 includes a frustoconical section 64 connected to a tabbed collar 66. Tabbed collar 66 has a pair of oppositely disposed tabs 68 defining a pair of oppositely disposed receiver channels 70. A stubshaft 72 extends from tabbed collar 66 and between tabs 68 and terminates in a beveled end 74. A circumferential groove 76 extends about stubshaft 66 proximate beveled end 74.

When elongated structure 26 in the rotating condition is urged into pedicle 14 beyond probe member 28, step-down hole 16 is thereby formed into the pedicle 14. Step-down hole 16 can be formed to any step-down depth "$D_{sd}$" along side-cutting reamer member 32 and up to and including cylinder portion 56 of end member 30. For the first exemplary embodiment of combination probe and reamer tool element 10 of the present invention, frustoconical section 64 of end member 30 acts as a stop preventing elongated structure 26 when in the rotating condition from any further entry into workpiece 14. Thus, variable depth "$D_v$" of trailing anchor hole 24 is limited by where frustoconical section 64 is located on elongated structure 26.

A second exemplary embodiment of a combination probe and reamer tool element 210 of the present invention is introduced in FIGS. 11–15. Combination probe and reamer tool element 210 comprises an elongated structure 226 having a probe member 228, an end member 230 and a reamer cutting member 232. Probe member 228 includes a blade portion 234 having a pair of oppositely disposed sidewalls 236 extending parallel with one another. Cutting member 232 has a plurality of cutting elements 246. Each of cutting elements 246 extends parallel with longitudinal axis "A". End member 230 includes a cylindrical portion 256 having an outer cylindrical surface 258 with indicia 260 formed thereon and a connecting end portion 262. As shown in FIG. 12, connecting end portion 262 extends from cylindrical portion 256 and has a pair of oppositely disposed connecting sidewalls 278 which extend parallel with one another. A bore 280 is formed through at least connecting end portion 262 which facilitates connection of elongated structure 226 to a conventional drill device having a quick connect and disconnect assembly.

FIG. 16 illustrates an alternative embodiment of a probe member 328 of the invention in association with the side-cutting reamer element 232. The probe member 328, as shown in FIG. 16, is generally cylindrical in cross-section, terminating in a rounded end 329. Probe 328 may be used in lieu of a probe 28 or 328 having a blade portion. If appropriate, a burr may be utilized to prepare a site on the cortical to receive the round-ended probe 328. As shown in FIG. 16, the cutting elements 346 are provided with narrow, flat or planar top 347 and are separated by similar planar surfaces 345.

The combination probe and reamer tool element of the present invention has been spawned from a need in the medical industry to reduce the incidence of pedicle perforation and consequent nerve injuries and at the same time to reduce the number of operative steps during spinal fixation surgery which are presently required under current techniques to insert pedicle screws into the pedicles of spinal vertebrae. With the present invention, pedicles of spinal vertebrae can now be probed to form a leading pilot hole and subsequently reamed to form a trailing anchor hole with the same combination probe and reamer tool element. The leading pilot hole and the trailing anchor hole form a single step-down hole in the pedicle. Also, the combination probe and reamer tool element has a quick-disconnect end. Now, the combination probe and reamer tool element can remain in the step-down hole and quickly disconnected from the drill device. While remaining in the step-down hole, the combination probe and reamer tool element can be also be used as an x-ray marker. Additionally, the combination probe and reamer tool element is calibrated with indicia so that the depth of the step-down hole being formed in the pedicle can be visually determined by an operating surgeon without the use of some other depth gauge. Given these advantages and benefits in a single tool element, the number of operative steps now required during spinal fixation surgery is reduced. This not only saves time for surgery but is also safer since a patent spends less time under anesthesia and avoid pedicle perforation and nerve injury.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A method for providing a screw hole in a pedicle, said pedicle having a relatively hard cortical outer portion and a relatively soft cancellous inner portion wherein said method comprises:

(i) providing a unitary instrument, said instrument having
   (a) an elongated probe member,
   (b) a side-cutting reamer member, and
   (c) an end member for rotatable connection to a rotating power source
       wherein said side-cutting reamer member is positioned between said probe member and said end member, and
       wherein said probe member, said reamer member and said end member rotate as a unit when said end member is operatively connected to an activated rotating power source;

(ii) identifying a location for a screw hole on the surface of said relatively hard cortical outer portion of said pedicle;

(iii) providing, at said location for a screw hole, an opening for said probe member in said relatively hard cortical outer portion of said pedicle;

(iv) introducing said probe member into said opening and urging said probe member to penetrate said relatively soft cancellous inner portion of said pedicle; and (v) rotating said unitary instrument,
    wherein probe and reamer member are self-centered to provide a screw hole in said pedicle, said self-centering being consequent from deflection, as said rotating proceeds, by said relatively hard outer cortical portion of said pedicle, of said elongated probe member and said side-cutting reamer member.

2. A unitary surgical instrument for providing a screw hole in a human pedicle, said pedicle having a relatively hard cortical outer portion and a relatively soft cancellous inner portion, said instrument having:

(a) an elongated probe member sized for penetration of said soft cancellous inner portion of said pedicle, (b) a side-cutting reamer member sized to define a portion of said screw hole in said relatively hard cortical outer portion of said pedicle, and (c) an end member for rotatable connection to a rotating power source, wherein said unitary instrument is self-centering as said unitary surgical instrument is rotated to provide said screw hole, said self-centering being consequent from deflection, by said relatively hard cortical outer portion of said pedicle, of said elongated probe member and said reamer member.

* * * * *